(12) United States Patent
Clapp et al.

(10) Patent No.: US 8,790,668 B2
(45) Date of Patent: Jul. 29, 2014

(54) PERSONAL CARE COMPOSITIONS THAT DEPOSIT SHINY PARTICLES

(75) Inventors: Mannie Lee Clapp, Mason, OH (US); Cynthia Ann Garza, Cincinnati, OH (US); Qing Stella, Cincinnati, OH (US); Paul Robert Tanner, Lebanon, OH (US); Rebecca Ann Taylor, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1146 days.

(21) Appl. No.: 10/841,301

(22) Filed: May 7, 2004

(65) Prior Publication Data

US 2004/0223993 A1   Nov. 11, 2004

Related U.S. Application Data

(60) Provisional application No. 60/468,953, filed on May 8, 2003, provisional application No. 60/469,570, filed on May 9, 2003, provisional application No. 60/514,962, filed on Oct. 28, 2003.

(51) Int. Cl.
| | | |
|---|---|---|
| *A61Q 1/02* | (2006.01) | |
| *A61Q 17/00* | (2006.01) | |
| *A61K 8/06* | (2006.01) | |
| *A61K 8/29* | (2006.01) | |
| *A61K 33/12* | (2006.01) | |
| *A01N 59/06* | (2006.01) | |

(52) U.S. Cl.
USPC ........ 424/401; 424/70.9; 424/70.12; 424/682; 424/683; 424/684

(58) Field of Classification Search
USPC .......................................... 424/401, 489, 490
See application file for complete search history.

(56) References Cited

U.S. PATENT DOCUMENTS

| | | | |
|---|---|---|---|
| 3,087,829 A | 4/1963 | Linton et al. | |
| 3,123,490 A | 3/1964 | Bolomey et al. | |
| 4,323,544 A | 4/1982 | Magder | |
| 5,223,559 A | 6/1993 | Arraudeau et al. | |
| 5,228,912 A | 7/1993 | Driller et al. | |
| 5,487,168 A | 1/1996 | Geiner et al. | |
| 5,661,189 A | 8/1997 | Grieveson et al. | |
| 6,132,873 A | 10/2000 | Dietz et al. | |
| 6,190,648 B1 | 2/2001 | Kouzu et al. | |
| 6,245,323 B1 | 6/2001 | Christie et al. | |
| 6,340,723 B1 | 1/2002 | Nita et al. | |
| 6,471,762 B1 | 10/2002 | Deluca, Jr. et al. | |
| 6,491,932 B1 | 12/2002 | Ramin et al. | |
| 6,645,511 B2 * | 11/2003 | Aronson et al. | 424/401 |
| 2003/0161805 A1 | 8/2003 | Schlossman et al. | |
| 2004/0048757 A1 | 3/2004 | Zhang et al. | |
| 2004/0048758 A1 | 3/2004 | Zhang et al. | |
| 2004/0105827 A1 | 6/2004 | Grimm et al. | |
| 2004/0223929 A1 * | 11/2004 | Clapp et al. | 424/63 |
| 2004/0234565 A1 | 11/2004 | Stella et al. | |

FOREIGN PATENT DOCUMENTS

| | | |
|---|---|---|
| EP | 1064918 B1 | 9/2002 |
| JP | 5-43431 A | 2/1993 |
| JP | 8-133928 A | 5/1996 |
| JP | 08188723 | 7/1996 |
| JP | 9-136815 A | 5/1997 |
| JP | 9-301826 A | 11/1997 |
| JP | 11193215 | 7/1999 |
| JP | 2000-063238 A | 2/2000 |
| JP | 2002-128639 A | 5/2002 |
| JP | 2002-138010 A | 5/2002 |
| JP | 2007-302583 A | 11/2007 |
| WO | WO 98/50471 A | 11/1998 |
| WO | WO 99/24001 A1 | 5/1999 |
| WO | WO 00/75240 A1 | 12/2000 |
| WO | WO 01/74979 A1 | 10/2001 |
| WO | WO 02/067888 A1 | 9/2002 |
| WO | WO 2004/024119 A1 | 3/2004 |

OTHER PUBLICATIONS silicone definition [online] retreived on Dec. 3, 2013 from: http://education.yahoo.com/reference/dictionary/entry/silicone.*
silane definition [online] retreived on Dec. 3, 2013 from: http://www.merriam-webster.com/dictionary/silane.*
Emmert, Dr. Ralf, "Quantification of the Soft-Focus Effect", Cosmetics & Toiletries, vol. 111, pp. 57-61 (Jul. 1996).
Treated Pigments—KOBO Technical Brochure, XP002299173 (May 2000) http://www.koboproductsinc.com/Downloads/TreatedPigments.pdf.
Special Effects Pigments—KOBO, XP002299376 (Jul. 24, 2003) http://www.koboproductsinc.com/SEP.html.
International Search Report PCT/US2004/014437 including Written Opinion of the International Searching Authority mailed Oct. 27, 2004, 15 pages.

* cited by examiner

*Primary Examiner* — Ernst Arnold

(57) ABSTRACT

The present invention relates to a personal care composition that contains a rinse-off composition which deposits at least 0.5 μg/cm² of shiny particles on the skin. Preferably, the shiny particles are hydrophobically modified interference pigments. The inventors have found that hydrophobically modifying the particles significantly improves the deposition of the particles on skin from rinsable compositions.

22 Claims, No Drawings

PERSONAL CARE COMPOSITIONS THAT DEPOSIT SHINY PARTICLES

CROSS REFERENCE TO RELATED APPLICATIONS

This application claims the benefit of Provisional application Ser. No. 60/468,953, filed May 8, 2003, of Provisional application Ser. No. 60/469,570, filed May 9, 2003, and of Provisional application Ser. No. 60/514,962, filed Oct. 28, 2003.

TECHNICAL FIELD

The present invention relates to the field of personal care compositions for improving appearance and feel of keratinous surfaces. More specifically, rinsable personal care compositions that deposit shiny particles on keratinous surfaces which provide excellent skin tone and radiance.

BACKGROUND OF THE INVENTION

Personal care compositions are well known and widely used. These compositions have long been employed to cleanse and moisturize skin, deliver actives, hide imperfections and to reduce the oiliness/shine associated with sebum. Personal care compositions have also been used to alter the color and appearance of skin.

These compositions generally incorporate organic or inorganic particulate material to reduce the shine or redness of skin, and to also cover over skin imperfections such as wrinkles. For example, emulsions may contain $TiO_2$ as an opacifying agent to provide a white appearance to the emulsion. Several publications have also disclosed the use of $TiO_2$ in personal care compositions. See, e.g. U.S. Pat. No. 5,223,559 and JP 08188723. In addition, R. Emmert has stated the desire to use optical means to formulate products that give the consumer an immediate, visual improvement (Dr. Ralf Emmert, Quantification of the Soft-Focus Effect, Cosmetics & Toiletries, Vol. 111, July 1996, pp. 57-61). Emmert discloses that one can mechanically fill in skin lines with a reflective substance such as $TiO_2$. However, Emmert teaches that such reflective materials result in an undesirable mask-like appearance.

To achieve pearlescent effect, interference pigments have been used for cosmetic applications. Mica, coated with varying thickness of titanium dioxide has been used to yield a pigment with a silvery, pearl-like effect. See, e.g. U.S. Pat. Nos. 3,087,829 and 3,123,490. Later teachings disclosed the use of thin film optics that resulted in pigments with brilliant luster and a broad range of interference colors and multicolour effect. See, e.g. U.S. Pat. Nos. 6,132,873 and 4,323,544.

Interference pigments have been developed for color cosmetics and skin care to provide luster and color effect. See, e.g. JP11193215, WO9924001 and WO200174979. However, since the surfaces of interference pigment are hydrophilic, they will remain in any aqueous phase present. As a result, they are do not associate with any oil phase present in a composition. This is often a desirable property when even dispersion of the pigments is desired to give the product a nacreous appearance.

While the compositions and disclosures of the prior art provide useful advances in the art of personal care compositions, there remains the need for improved rinse off compositions that deliver immediate improvements in appearance and skin feel that will effectively deposit shiny particles on all parts of the body. The compositions also need to be non-greasy and easy to apply. Therefore, it is desirable to provide a topical rinse off composition comprising a select level and blend of shiny particles to provide a unique level of light reflectance and color shift to increase the radiance across all skin types. Furthermore, it is desirable to provide a personal care composition comprising shiny particles to maximize sheen and lustre on the skin. It is also desirable to provide personal care compositions that effectively provide skin moisturization. It is further desirable to deliver the above skin conditioning and appearance benefits via an in-the-shower or in-the-bath lotion. Unfortunately, in the shower/bath, moisturizers are often readily rinsed from the skin. This is particularly true when surfactant is present. Therefore, a need still exists for a rinsable personal care composition that effectively deposits shiny particles.

SUMMARY OF THE INVENTION

The inventors have surprisingly found that rinsable personal care compositions that contain modified shiny particles and a dispersed oil phase will effectively deposit shiny particles on the skin in the shower and/or bath. Additionally, modified shiny particles provide radiance across all skin types. The present invention relates to a personal care composition that comprises a rinse-off composition which deposits at least 0.5 µg/cm² shiny particles on the skin. The present invention provides personal care compositions, which may further comprise skin benefit agents. These compositions provide improved skin appearance, aesthetics and skin feel during and/or after application, and are useful in providing improved deposition to the desired area of the skin.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods. It should be obvious to one skilled in the art that other common personal care materials can be incorporated without altering the substance of the invention.

All publications cited herein are hereby incorporated by reference in their entirety.

The term "dermatologically-acceptable," as used herein, means that the compositions or components thereof so described are suitable for use in contact with human skin without undue toxicity, incompatibility, instability, allergic response, and the like.

The term "hydrophobically modified interference pigment" or "HMIP", as used herein, means a portion of the interference pigment surface has been coated with a hydrophobic material.

The term "hydrophobically modified shiny particle" "HMSP" as used herein means, the shiny particle surface has been hydrophobically modified from its native state or a shiny particle which is naturally hydrophobic.

The term "interference pigment", as used herein, means a pigment with pearl gloss prepared by coating the surface of a particle substrate material (generally platelet in shape) with a thin film. The thin film being a transparent or semitransparent material having a high reflective index. The metal oxide shows a pearl gloss resulting from mutual interfering action between reflection and incident light from the platelet substrate/coating layer interface and reflection of incident light from the surface of the coating layer.

The term "rinsable composition" as used herein, means a composition designed to be rinsed off by a liquid such as water. After the composition is rinsed off, pigments are deposited on the skin and the skin radiance is realized.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

The term "shiny particle" as used herein, means that a particle which exhibits specular reflection due to a platelet shape. Specular reflection refers to the phenomena where an incident beam of light is reflected at the equal and opposite angle to the angle of incidence.

The term "topical application", as used herein, means to apply or spread the compositions of the present invention onto the surface of the skin.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The compositions of the invention are useful for topical application and for providing an essentially immediate (i.e., acute) visual improvement in skin appearance following rinse off of the composition from the keratinous surface. Without intending to be limited by theory, it is believed that this acute skin appearance improvement results at least in part from therapeutic coverage or masking of skin imperfections by the hydrophobically modified shiny particles. The compositions provide the visual benefits without imparting an unacceptable skin appearance such as skin whitening.

Pigment Deposition Tape Strip Method

The Pigment Deposition Tape Strip Method can be used to semi-quantitatively determine deposition of shiny particles onto keratinous surfaces. The method employs the use of a tape strip for removing particles from skin and imaging these particles for a quantitation of deposited particles.

The first step is to weigh 1 g of pigment that is the same as those in the product being tested in a vial. Next, 9 g melted petrolatum is added and mixed well with a spatula.

Weigh out 994.17 g purified water (Millipore or equivalent). While mixing @ ~600-700 rpm using a Lightning Laboratory Stirrer or Heidolph 2051 mixer and appropriate blade, to the water slowly add 3.50 g Pemulen TR-1 (BF Goodrich) so as to prevent clumping. Follow this with 30 minutes of stirring to ensure complete hydration of Pemulen. To the mixture, while still stirring slowly, add 2.33 g TEA (Triethanolamine 99%-Dow Chemical). Follow this by an additional 30 minutes of stirring to ensure homogeneity.

Evaluate product for separation after standing for 1 hour. Separation is not acceptable. Store in glass jars at room temperature. Now, mix 1 ml of the pigment/petrolatum mixture with 19 ml of 0.35% Pemulen Gel mixture, using Cito Unguator on speed 8 (~2050 rpm) for 4 minutes. This combination of the 1 ml of the pigment/petrolatum mixture with 19 ml of 0.35% Pemulen Gel mixture will be used to evaluate deposition of pigment on the skin.

Wash inner arms of subject with Olay Sensitive Skin bar and warm water, rinsing until all soap has been removed. Dry with clean paper towels. Mark inner arms of subject with three 4×6 cm sites per arm. Apply to site #1 (upper left, nearest elbow) 5 µl of the mixture described previously, spreading evenly over site and rubbing in with gloved finger for ~20 seconds covering entire site. This application equals 1 µg pigment per $cm^2$. Apply to site #2 (middle left) 24 µl of mixture described previously, spreading evenly over site and rubbing in with gloved finger for ~20 seconds covering entire site. This application equals 5 µg pigment per $cm^2$. Apply to site #3 (bottom left, nearest wrist) 48 µl of mixture described previously. This equals 10 µg per $cm^2$. Apply to site #4 (top right, nearest elbow) 96 µl of mixture described previously. This equals 20 µg per $cm^2$. Let sites air dry for a minimum of 10 min. Apply to site #5 (middle right) 96 µl of the product being tested. Apply to site #6 (bottom right, nearest wrist) 96 µl of the product being tested. Rinse each site #5 and #6 with warm tap water for 10 seconds each, not contaminating one site with the next while rinsing. Then pat each site dry gently with clean paper towels, again not contaminating one site with the next.

Take approximately 1" of Scotch Tape and apply to site #1. Rub over the top of the applied tape to pick up product below. Remove the tape and reapply same tape to very same previously stripped area, so as to pull product from area twice on the same tape. Then secure this stripping tape to a clean microscope slide, product side up, marking the slide as "1 µg/$cm^2$". Repeat the application of Scotch Tape method described previously for sites #2 through #6 (in that order), marking each slide appropriately.

Take microscope images of each tape strip that are made with a 10× objective and top lighting.

Visually compare the numbers of pigment particles in sites #5 and #6 images with those in the standard sites #1 through #4 images and give a deposition level. The deposition level is the number of observed particles per $cm^2$ (for example, 8 µg/$cm^2$). Take an average of the observations of sites #5 and #6 from at least 3 people.

Pigment Deposition by X-ray Fluorescence Method

The Pigment Deposition by X-ray Fluorescence Method can be used to quantitatively determine deposition of shiny particles onto keratinous surfaces. The product containing pigments is applied to the inner forearm according to the following procedure. The forearm from the elbow to the wrist is rinsed for 5 seconds using 95° F. city water at a flowrate of 50-60 mL/sec. A wetted Ivory soap bar is rotated in both hands for 6 full rotations, the lather is gathered and applied to the inner forearm using 10 full back and forth strokes. The lather is rinsed from the forearm for 10 seconds after which 1.0 mL of product is dispensed from a 1-mL syringe and rubbed into the inner forearm for 10 seconds. The product is left on the forearm for 10 seconds and then the forearm rinsed with water for 10 seconds. The forearm is patted dry with a paper towel.

Deposited pigment is recovered from the forearm by using the following tape-stripping procedure. A standard D-Squame tape (22-mm diameter, CuDerm Corporation, Dallas, Tex.) is firmly placed on the inner forearm at least 2 inches from the elbow crease, if possible. The location of the first tape is marked with a Sharpie by placing four equally spaced points around the tape. The tape strip is removed with Teflon-coated tweezers and placed in its own individual pre-labeled container (e.g., a disposable petri dish) with the adhesive side of the tape facing up. Subsequent tapes were placed firmly within the marked area and collected in the same manner until a total of 10 tapes were collected per site.

A Philips Analytical model PW2404 4000-Watt wavelength-dispersive X-ray fluorescence (XRF) instrument (PANalytical formerly Philips Analytical, Almelo, Netherlands) is used to quantify the amount of interference pigment on each D-Squame tape. Each tape is placed into a sample pan with the adhesive side facing up and subjected to X-ray radiation (Rhodium anode operated at 37 kV and 108 mA). The intensity of X-ray emission from titanium (K□ line) is detected, LiF 200 crystal, flow detector, 2□=86.1780° for 16 seconds) and used to quantify the mass of interference pigment on each tape strip based on a linear calibration curve of emission intensity versus pigment mass. The mass of pigment deposited per unit area is calculated by summing the mass of pigment on each of the 10 tape strips collected per site and dividing by the area of the tape strip sampled by the XRF instrument (2.01 cm$^2$).

Calibration standards were generated by accurately weighing to the nearest 0.0002 g the appropriate interference pigment (or mixture of interference pigments) into a flask and dispersing the interference pigment in a known volume of acetone. Seven calibration solutions were made for each interference pigment (or mixture of interference pigments) ranging in concentration from 100 to 3600 □g/mL. Each standard is stirred for at least one hour with a Teflon-coated magnetic stir bar. While maintaining stirring, 40 □L of each calibration standard is spiked onto the center of a D-Squame tape strip by using a positive displacement pipet. To generate the calibration curve, each of the 7 calibration standards is analyzed in triplicate and the titanium X-ray emission intensity is plotted versus the mass of pigment spiked onto the tape.

Particle Contact Angle Test

The Particle Contact Angle Test is used to determine hydrophobicity of shiny particles. The greater the contact angle the greater the hydrophobicity of the particle.

A Spectra-Tech Qwik Handi-Press (Thermo Nicolet, Madison, Wis.) is used to compress the powder into 7-mm diameter discs. After applying firm hand pressure, the compression is held for 1 min prior to releasing pressure and removing the disc. The disc is examined for smoothness and rejected unless the surface is smooth. First Ten Angstrom FTÅ200 (First Ten Angstrom, Portsmouth, Va.) contact angle analyzer is employed to determine advancing and receding contact angles. A drop of 7 microliters of water (Millipore, Milli Q deionized, distilled) is dangled from the needle and slowly placed on the middle of the disc. The needle is left inserted in the drop but not in contact with disc. 0.1 microliters/second of water is pumped into the drop. Contact angle images were captured every 0.1 sec. until the maximum contact angle is obtained. The process is reversed to determine the receding contact angle in that the needle is left in the drop and fluid is removed at 0.1 microliters/second until the minimum contact angle is obtained. Images were obtained at 0.1 images/second, then calculate the contact angle. To calculate the contact angle, a curve is fitted to the profile of the drop on both sides. The baseline is drawn across the drop. The intersection of the curves and baseline is determined on both sides of the drop. The tangent (slopes) of the curve at the intersection is determined on both sides of the drop. The contact angle is the angle between the baseline and the tangent interior to the drop. The average contact angle is determined from the contact angles from both sides of the drop.

Dispersed Oil Phase

The dispersed oil phase comprises a skin compatible oil. By definition, the dispersed oil phase will have negligible solubility in the external phase and will be present as discrete particles in the composition. The dispersed oil phase preferably comprises no more than about 80 weight percent of the composition, more preferably no more than about 70 weight percent, still more preferably no more than about 60 weight percent, and still more preferably no more than about 50 weight percent of the dispersed oil phase. The dispersed oil phase preferably comprises at least about 1 weight percent, more preferably at least about 5 weight percent, even more preferably at least about 7 weight percent, and still more preferably at least 10% of the composition.

The shear index is a measure of how shear thinning the materials are as described in the Lipid Rheology method described herein. It is preferred that the skin compatible oil be shear thinning either by virtue of its composition or the structurants that may be added. Preferably, the shear index of the dispersed oil phase will preferably be less than 0.9, more preferably less than 0.75, even more preferably less than 0.6, even more preferably less than 0.45, and still more preferably less than 0.3.

Skin Compatible Oils

A skin compatible oil is defined here, as an oil that is liquid or semi-solid at the temperature at which bathing is carried out that is deemed safe for use in cosmetics being either inert to the skin or actually beneficial. The most useful skin compatible oils for the present invention include ester oils, hydrocarbon oils, and silicone oils.

Ester oils as the name implies have at least one ester group in the molecule. One type of common ester oil useful in the present invention are the fatty acid mono and polyesters such as cetyl octanoate, octyl isonanoanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like.

A second type of useful ester oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by Finetex as Finsolv are also suitable, as is ethylhexanoic acid glyceride.

A third type of ester oil is liquid polyester formed from the reaction of a dicarboxylic acid and a diol. An example of polyesters suitable for the present invention is the polyesters marketed by Exxon Mobil under the trade name PURESYN ESTER.®.

A second class of skin compatible oils suitable for the present invention is liquid and semi-solid hydrocarbons. These include linear and branched oils such as liquid paraffin, squalene, squalane, mineral oil, low viscosity synthetic hydrocarbons such as polyalphaolefin sold by Exxon Mobil under the trade name of PURESYN PAO and polybutene under the trade name PANALANE or INDOPOL. Light (low viscosity) highly branched hydrocarbon oils are also suitable.

Petrolatum is a unique hydrocarbon material and a useful component of the present invention. Its semi-solid nature can be controlled both in production and by the formulator through blending with other oils.

A third class of useful skin compatible oils is silicone based. They include linear and cyclic polydimethyl siloxane, organo functional silicones (alkyl and alkyl aryl), and amino silicones.

Shiny Particles

The shiny particles of the compositions are platelets with a smooth surface. Each smooth surface behaves like a tiny mirror, in contrast to a rough or non-planar surface that reflects light in a diffuse manner. Furthermore, the shiny particles of the present invention include interference pigment, natural pearlescent pigment, natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and metallic pigment. The shiny particles have a Relative Index (RI) of at least 1.2, preferably greater than 1.3, even more preferably greater than 1.4, still more preferably greater than 1.5. The shiny particles of the personal care compositions preferably comprise no more than about 20 weight percent of the composition, more preferably no more than about 10 weight percent, even more preferably no more than about 7 weight percent, and still more preferably no more than about 5 weight percent of the personal care composition. The shiny particle of the personal care composition preferably comprises at least about 0.01 weight percent of the personal care composition, more preferably at least about 0.05 weight percent, even more preferably at least about 0.1 weight percent, and still more preferably at least about 0.2 by weight of the composition. The shiny particles of the present invention can be hydrophobic or hydrophobically modified.

The Particle Contact Angle Test of the present invention is used to determine contact angle of shiny particles. The greater the contact angle the greater the hydrophobicity of the shiny particle. The shiny particles of the present invention possess a contact angle of at least 60 degrees, more preferably greater than 80 degrees, even more preferably greater than 100 degrees, still more preferably greater than 110 degrees, even still more preferably greater than 120 degrees, even still even more preferably greater than 130 degrees, even still even more preferably greater than 140 degrees, and even still even more preferably greater than 180 degrees.

Interference Pigment

An interference pigment is a pigment with pearl gloss prepared by coating the surface of a particle substrate material (generally platelet in shape) with a thin film. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. When pigment is applied and rinsed as described in the Pigment Deposition Tape Strip Method, the deposited pigment on the skin is preferably at least 0.5 µg/cm², more preferably at least 1 µg/cm², and still more preferably at least 5 µg/cm².

In a preferred embodiment of the present invention the interference pigment surface is hydrophobic or has been hydrophobically modified. The hydrophobically modified interference pigment or HMIP allows for the entrapment of the HMIP within the dispersed phase and greater deposition of the HMIP. In a preferred embodiment of the present invention, the invention contains both HMIPs and a dispersed oil phase. Preferably the ratio of HMIP to dispersed oil phase is 1:1 to about 1:70, more preferably 1:2 to about 1:50, still more preferably 1:3 to about 1:40 and even more preferably 1:7 to about 1:35.

When formulated into a product, the HMIP's are preferably entrapped within the dispersed oil phase. This would require that the oil phase particle size is generally larger than the HMIP. In a preferred embodiment of the invention, the oil phase particles contain only a small number of HMIPs per oil particles. Preferably this is less than 20, more preferably less than 10, still more preferably less than 5. These parameters, the relative size of the oil droplets to the HMIP and the approximate number of HMIP particles per dispersed oil particles, can be determined by using visual inspection with light microscopy.

The HMIP and the oil can be mixed into the composition via a premix or separately. For the case of separate addition, the hydrophobic pigments partition into the oil phase during the processing of the formulation. The HMIP of the present invention preferably has a hydrophobic coating comprising no more than about 20 weight percent of the total particle weight, more preferably no more than about 15 weight percent, even more preferably no more than about 10 weight percent. The HMIP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

The interference pigments of the present invention are platelet particulates. The platelet particulates of the personal care compositions preferably have a thickness of no more than about 5 µm, more preferably no more than about 2 µm, still more preferably no more than about 1 µm. The platelet particulates of the personal care composition preferably have a thickness of at least about 0.02 µm, more preferably at least about 0.05 µm, even more preferably at least about 0.1 µm, and still more preferably at least about 0.2 µm.

The particle size determines the opacity and luster. The particle size is determined by measuring the diameter thickness of the particulate material. The term "diameter," as used herein, means the largest distance across the major axis of the particulate material. Diameter can be determined by any suitable method known in the art, such as particle size analyzer Mastersizer 2000 manufactured by Malvern Instruments. The interference pigment of the personal care compositions preferably have an average diameter not greater than about 200 µm, more preferably not greater than 100 µm, even more preferably not greater than about 80 µm, still more preferably not greater than than about 60 µm. The interference pigment of the personal care compositions preferably have a diameter of at least about 0.1 µm, more preferably at least about 1.0 µm, even more preferably at least about 2.0 µm, and still more preferably at least about 5.0 µm.

The interference pigment of the personal care compositions comprises a multiple layer structure. The center of the particulates is a flat substrate with a refractive index (RI) normally below 1.8. A wide variety of particle substrates are useful herein. Nonlimiting examples are natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, preferably mica, silica and alumina flakes.

A layer of thin film or a multiple layer of thin films are coated on the surface of a substrate described above. The thin films are made of highly refractive materials. The refractive index of these materials is normally above 1.8.

A wide variety of thin films are useful herein. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, preferably $TiO_2$, $Fe_2O_3$, $Cr_2O_3 SnO_2$. For the multiple layer structures, the thin films can be consisted of all high refractive index materials or alternation of thin films with high and low RI materials with the high RI film as the top layer.

The interference color is a function of the thickness of thin film, the thickness for a specific color may be different for different materials. For $TiO_2$, a layer of 40 nm to 60 nm or a whole number multiple thereof gives silver color, 60 nm to 80 nm yellow color, 80 nm to 100 nm red color, 100 nm to 130 nm blue color, 130 nm to 160 nm green color. In addition to the interference color, other transparent absorption pigments can be precipitated on top of or simultaneously with the $TiO_2$ layer. Common materials are red or black iron oxide, ferric ferrocyanide, chromium oxide or carmine. It was found that the color of the interference pigment in addition to its brightness had a significant influence on human perception of skin tone. In general, preferred colors are silver, gold, red, green and mixtures thereof.

Nonlimiting examples of the interference pigments useful herein include those supplied by Persperse, Inc. under the trade name PRESTIGE®, FLONAC®; supplied by EMD Chemicals, Inc. under the trade name TIMIRON®, COLORONA®, DICHRONA® and XIRONA®; and supplied by Engelhard Co. under the trade name FLAMENCO®, TIMICA®, DUOCHROME®.

A second class of interference pigment is based on cholesteric liquid crystal, e.g. HELICONE® HC supplied by KOBO products. HELICONE® HC is composed of transparent platelets of polyacrylates with a helical superstructure. As part of this structure, cigar-shaped liquid crystal molecules are fixed into layers of parallel rows. Each layer has a slightly different molecular orientation and the distance between two layers with the same molecular orientation defines as the "pitch", which determines the color. This type pigment is hydrophobic. Therefore, they can be used without surface treatment.

Metallic pigment is also useful herein. The higher electronic energy levels of a metal are characterised by an essentially continuous band of allowed energies. This means that all incident radiation can be absorbed. However, each excited electron can immediately fall back to the state that it came from, emitting exactly the same energy, causing a flat piece of metal to appear reflective. Therefore, reflectivity is a better term than refractive index to describe the shininess of metals. "Reflectivity (R)" is defined for light perpendicularly on a metal surface as:

$$R=[(n-1)^2+k^2]/[(n+1)^2+k^2]$$

Where n is the refractive index and k is termed the extinction coefficient, coefficient of absorption or attenuation coefficient. For a metal both k and n are strongly wavelength dependent. (Richard Tilley, "Colour and the optical properties of materials" Wiley). The "high reflectivity" of the metallic pigment in the present invention means at least 0.6 at a selected wavelength.

Unlimiting examples of the metallic pigment useful herein include those supplied by Persperse, Inc. under the trade name VISIONAIRE®. The particle sizes and concentration used in the compositions are similar to those for the interference pigment.

Aqueous Phase

The continuous aqueous phase of the present invention typically comprises from no more than 90% of a fluid, preferably no more than 80%, even more preferably no more than 70%, still more preferably no more than 60%. The continuous aqueous phase of the present invention typically comprises at least 10% of a fluid, preferably at least 20%, even more preferably at least 30%, still more at least 40% of a fluid. The term "fluid" as used herein means water, mono- and polyhydric alcohols (glycerin, propylene glycol, ethanol, isopropanol, sorbitol, etc.), or any material which is water miscible.

Optional Ingredients

The compositions of the present invention may contain one or more additional skin care components. In a preferred embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The CTFA *Cosmetic Ingredient Handbook*, Second Edition (1992) describes a wide variety of nonlimiting cosmetic and pharmaceutical ingredients commonly used in the personal care industry, which are suitable for use in the compositions of the present invention.

In any embodiment of the present invention, however, the additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

Structurants

The present invention may optionally comprise an oil structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec−1, preferably 200 to about 100,000 poise, and most preferably 200 to about 50,000 poise as determined using the lipid rheology method described below. The amount of structurant required to produce this viscosity will vary depending on the oil and the structurant, but in general, the structurant will preferably be at most 75% of the dispersed oil phase, more preferably at most 50%, and still more preferably at most 35% of the dispersed oil phase.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

Surfactants

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Suitable surfactants include those selected from the group consisting of anionic surfactants, nonionic surfactants, amphoteric surfactants, and mixtures thereof. Non-limiting examples of surfactants useful in the compositions of the present invention are disclosed in U.S. Pat. No. 6,280,757, to McAtee et al., issued Aug. 28, 2001.

A) Anionic Surfactants

Non-limiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

B) Non-Ionic Surfactants

Non-limiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

C) Amphoteric Surfactants

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

D) Non-Lathering Surfactants

A wide variety of non-lathering surfactants are useful herein. The composition of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

E) Emulsifier Systems

In addition, there are several commercial emulsifier mixtures that are useful in some embodiments. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl)-N—N-Dimethyl,N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse.

Thickening/Aqueous Phase Stability Agents

The compositions of the present invention, in some embodiments, may further include one or more thickening/aqueous phase stability agents. When present, the thickening/aqueous phase stability agent preferably comprises no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the Stability Agent is to say that it must build viscosity in the product. This can be measured using the Stability Agent Viscosity Test. Preferably, the stability agent produces a viscosity in this test of at least 1000 cps, more preferably at least 1500 cps, and still more preferably at least 2000 cps.

Nonlimiting examples of thickening agents useful herein include carboxylic acid polymers such as the carbomers (such as those commercially available under the tradename CARBOPOL® 900 series from B.F. Goodrich; e.g., CARBOPOL® 954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL® 1342, CARBOPOL® 1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500 W, SSSA100H, from Lipo Chemicals, Inc., (Patterson, N.J.).

Another nonlimiting class of thickening agents useful herein are the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the tradename NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another nonlimiting class of thickening agents useful herein are the gums. Nonlimiting examples of gums useful herein include hectorite, hydrated silica, xantham gum, and mixtures thereof.

Yet another nonlimiting class of thickening agents useful herein are the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth-25 Methacrylate Crosspolymer) from Clariant and cationic stabylens.

Cationic Polymers

The present invention may also contain organic cationic deposition polymer Concentrations of the cationic deposition polymer preferably range from about 0.025% to about 3%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Nonlimiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymerin the personal care composition ranges from about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other Optional Ingredients

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); anti-oxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol) and anti-bacterial agents and mixtures thereof. These materials can be used at ranges sufficient to provide the required benefit, as would be obvious to one skilled in the art.

Analytical Methods

Lipid Rheology Test

Lipid rheology is measured on a TA Instruments AR2000 stress-controlled rheometer with a Peltier temperature controlled sample stage or an equivalent. A parallel plate geometry is used with a 40 mm plate and a 1 mm gap. The lower plate is heated to 85° C. and the melted lipid and structurant (if present) is added onto the lower plate and allowed to equilibrate. The upper plate is then lowered to the 1 mm gap while ensuring the lipid fills the gap fully, spinning the top plate and adding more lipid to promote wicking, and the sample is cooled quickly to 25° C. and equilibrated at 25° C. for 5 minutes. Viscosity is then measured using a stress-ramp procedure common on these types of machines using a logarithmic stress ramp from 20 to 2000 Pa at a rate of 60 seconds per decade (2 minute ramp test), with 20 measurements points per decade. The starting and ending stress is sufficient to induce flow and reach a shear rate of at least 10 sec−1. Viscosity is recorded and the data fitted to a power law model using Equation 1. Only points between 0.001 sec−1 and 40 seconds−1 are to be used in the power law fit. The viscosity at 1.0 sec−1 is calculated from Equation 1. One should carefully watch the sample during the test so that when the material is ejected from under the plate, the method is stopped.

Viscosities are recorded and the data fit to a power law with the following Equation 1:

$$\eta = \kappa \cdot \gamma(dot)^{(n-1)}$$

where $\eta$=viscosity, $\kappa$ is the consistency and $\gamma(dot)$ is the shear rate, and n is the shear index.

The viscosity at 1 sec−1 is then calculated using the calculated values of $\kappa$ and n from the fitted data.

Stability Agent Viscosity Test:

The polymeric stabilizer phase is formed using the ratio of stabilizer to water that will be found in the particular formulation of interest. For example, if the formulation contains 3 parts stabilizing polymer and 72 parts water, the ratio will be 1:24. The polymer is hydrated in the water phase at the appropriate ratio. The method of hydration will vary depending upon the polymer type, and may require high shear, heating, and/or neutralization. In any event, the polymer should be properly hydrated according to manufacturer's instructions. Once the polymer is fully hydrated, the system is allowed to sit at room temperature for at least 24 hours. After the resting period, the viscosity of the stabilizer phase is measured with a Brookfield or similar viscometer using a cone and plate (Spindle 41 for a Brookfield model DV II+) geometry at 1 sec−1 and 25 C. 2 ml of the product is placed in the cup of the viscometer and attached to the unit. The rotation is started and after 2 minutes the viscosity is recorded.

Lather Volume

Lather volume of a personal care composition can be measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal care composition is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total cleansing, treatment compositions, unless otherwise specified.

| Ingredient | Ex. 1 wt % | Ex. 2 wt % | Ex. 3 wt % | Ex. 4 wt % | Ex. 5 wt % | Ex. 6 wt % | Ex. 7 wt % | Ex. 8 wt % |
|---|---|---|---|---|---|---|---|---|
| I. Aqueous Phase Composition | | | | | | | | |
| Hydroxypropyl Starch Phosphate (Structure XL from National Starch) | 3.5 | 4.0 | 3.5 | 3.5 | 3.5 | 3.0 | 3.5 | 3.5 |
| Emulsifying Wax NF (Polawax from Croda) | 2.75 | 3.0 | 2.75 | | 2.75 | 2.5 | | 2.75 |
| Behenetrimonium methosulfate and cetearyl alcohol (Incroquat Behenyl TMS from Croda) | | | | 2.25 | | | 2.0 | |
| Fragrance | 1.0 | 1.0 | 1.0 | 1.0 | 1.0 | 1.0 | 1.0 | 1.0 |
| Preservatives | 0.8 | 0.8 | 0.8 | 0.8 | 0.8 | 0.8 | 0.8 | 0.8 |
| Water | Q.S. | Q.S. | Q.S. | Q.S. | Q.S. | Q.S. | Q.S. | Q.S. |
| II. Lipid/HMIP phase Composition | | | | | | | | |
| Petrolatum (Superwhite Protopet from WITCO) | 15 | | | | 5 | 15 | 15 | 15 |
| Mineral Oil (Hydrobrite 1000 PO White MO from WITCO) | | 20 | | | | 2 | | |
| Dimethicone Fluid (Dow Corning Silicone Fluid 10000 cst) | | | 10 | | | | 5 | |
| Puresyn 101LT (Polydecene from Exxon Mobile) | | | | 15 | | | | |
| Sunflower Seed Oil (Lipovol Sun from Lipo) | | | | | 10 | | | 5 |
| Mica/Titanium Dioxide/Dimethicone (SAT-Timiron MP115 Starluster from US Cosmetics) | 0.75 | | 1 | | 1.0 | 0.5 | | |
| Mica/Titanium Dioxide/Triethoxy caprylylsilane/Iron Oxide/Tin Oxide (Kobopearl Vibrant Gold-11S2 from Kobo Products Inc.) | | | | | | | | |
| Mica/Titanium Dioxide/Triethoxy caprylylsilane (Kobopearl Stellar White-11S2 from Kobo Products Inc.) | | | | | | | | |
| Titanium Dioxide/Mica/Silica/Dimethicone (SAT-Timiron Splendid Red from US Cosmetics) | 0.75 | 0.75 | | 2.0 | | | | |
| Mica/Titanium Dioxide/Tin Oxide/Triethoxy caprylylsilane (Kobopearl Interval Gold-11S2 from Kobo Products Inc.) | | | | | | | | |
| Mica/Titanium Dioxide/Tin Oxide/Triethoxy caprylylsilane (Kobopearl Interval Red-11S2 from Kobo Products Inc.) | | | | | | | | |

| Ingredient | | | | |
|---|---|---|---|---|
| Mica/Mineral/Titanium Dioxide/Iron Oxide/Lecithin (LT-Colorona Red Gold from US Cosmetics) | | 0.5 | | |
| Mica/Titanium Dioxide/Dimethicone (SAT-Timiron Super Green from US Cosmetics) | | 0.5 | | |
| Mica/Dimethicone (SA-M-M from US Cosmetics | | | | |
| Mica/Titanium Dioxide/Dimethicone (SAT-Flamenco Ultra Silk 2500 from US Cosmetics) | | | 0.5 | |
| Polyacrylate-4 (Helicone HC Maple from Kobo Products, Inc.) | | | | 2.0 |

| Ingredient | Ex. 9 wt % | Ex. 10 wt % | Ex. 11 wt % | Ex. 12 wt % |
|---|---|---|---|---|
| I. Aqueous Phase Composition | | | | |
| Hydroxypropyl Starch Phosphate (Structure XL from National Starch) | 3.5 | 3.75 | 3.75 | 3.75 |
| Emulsifying Wax NF (Polawax from Croda) | 2.75 | 2.75 | 2.75 | 2.75 |
| Behenetrimonium methosulfate and cetearyl alcohol (Incroquat Behenyl TMS from Croda) | | | | |
| Fragrance | 1.0 | 1.0 | 1.0 | 1.0 |
| Preservatives | 0.8 | 0.8 | 0.8 | 0.8 |
| Water | Q.S. | Q.S. | Q.S. | Q.S. |
| II. Lipid/HMIP phase Composition | | | | |
| Petrolatum (Superwhite Protopet from WITCO) | 20 | 20 | 15 | 20 |
| Mineral Oil (Hydrobrite 1000 PO White MO from WITCO) | | | 5 | 5 |
| Dimethicone Fluid (Dow Corning Silicone Fluid 10000 cst) | | | | |
| Puresyn 101LT (Polydecene from Exxon Mobile) | | | | |
| Sunflower Seed Oil (Lipovol Sun from Lipo) | | | | |
| Mica/Titanium Dioxide/Dimethicone (SAT-Timiron MP115 Starluster from US Cosmetics) | | | | |
| Mica/Titanium Dioxide/Triethoxy caprylylsilane/Iron Oxide/Tin Oxide (Kobopearl Vibrant Gold-11S2 from Kobo Products Inc.) | | 0.125 | 0.125 | |
| Mica/Titanium Dioxide/Triethoxy caprylylsilane (Kobopearl Stellar White-11S2 from Kobo Products Inc.) | | 0.25 | | 0.5 |
| Titanium Dioxide/Mica/Silica/Dimethicone (SAT-Timiron Splendid Red from US Cosmetics) | | | | |
| Mica/Titanium Dioxide/Tin Oxide/Triethoxy caprylylsilane (Kobopearl Interval Gold-11S2 from Kobo Products Inc.) | | 0.125 | 0.375 | |

| Ingredient | | |
|---|---|---|
| Mica/Titanium Dioxide/Tin Oxide/Triethoxy caprylylsilane (Kobopearl Interval Red-11S2 from Kobo Products Inc.) | | 0.5 |
| Mica/Mineral/Titanium Dioxide/Iron Oxide/Lecithin (LT-Colorona Red Gold from US Cosmetics) | | |
| Mica/Titanium Dioxide/Dimethicone (SAT-Timiron Super Green from US Cosmetics) | | |
| Mica/Dimethicone (SA-M-M from US Cosmetics | 3.0 | 3.0 |
| Mica/Titanium Dioxide/Dimethicone (SAT-Flamenco Ultra Silk 2500 from US Cosmetics) | | |
| Polyacrylate-4 (Helicone HC Maple from Kobo Products, Inc.) | | |

The personal care composition of Example 1-12 can be prepared by conventional formulation and mixing techniques.

Prepare the aqueous phase composition by first dispersing the hydroxypropyl starch phosphate in water. Add and heat the emulsifying wax is to 160 F. Next, Place the mixing vessel in a water bath to cool to under 100 F. Add fragrance.

Prepare the lipid phase by first premixing the HMIP(s) if necessary. Then, add the HMIP(s) to the lipid to the premix at 160 F. Then, add the lipid/HMIP phase to the aqueous phase (<80 F) with increased agitation. Add preservatives and agitate until product is smooth.

| Ingredient | Ex 13 wt % | Ex 14 wt % | Ex 15 wt % | Ex 16 wt % | Ex 17 wt % |
|---|---|---|---|---|---|
| I. Cleansing Phase Composition | | | | | |
| Miracare SLB-365 (from Rhodia) (Sodium Trideceth Sulfate, Sodium Lauramphoacetate, Cocamide MEA) | 47.4 | 47.4 | 47.4 | 47.4 | 47.4 |
| Guar Hydroxypropyltrimonium Chloride (N-Hance 3196 from Aqualon) | 0.7 | 0.7 | 0.7 | 0.7 | 0.7 |
| PEG 90M (Polyox WSR 301 from Dow Chemical) | 0.2 | 0.2 | 0.2 | 0.2 | 0.2 |
| Sodium Chloride | 3.5 | 3.5 | 3.5 | 3.5 | 3.5 |
| Preservatives | 0.84 | 0.84 | 0.84 | 0.84 | 0.84 |
| Citric Acid | 0.4 | 0.4 | 0.4 | 0.4 | 0.4 |
| Perfume | 2.0 | 2.0 | 2.0 | 2.0 | 2.0 |
| Expancel 091 DE 40 d30 (from Expancel, Inc.) | 0.4 | 0.4 | 0.4 | 0.4 | 0.4 |
| Water | Q.S. | Q.S. | Q.S. | Q.S. | Q.S. |
| (pH) | (6.0) | (6.0) | (6.0) | (6.0) | (6.0) |
| II. Lipid phase Composition | | | | | |
| Petrolatum (Superwhite Protopet from WITCO) | 74.58 | 74.58 | 74.58 | 74.58 | 74.58 |
| Mineral Oil (Hydrobrite 1000 PO White MO from WITCO) | 23.92 | 23.92 | 23.92 | 23.92 | 23.92 |
| Mica/Dimethicone | | 1.5 | | 1.5 | |
| Titanium Dioxide/Mica/Silica/Dimethicone (SAT-Timiron Splendid Red from US Cosmetics) | | | | | 0.75 |
| Mica/Titanium Dioxide/Tin Oxide/Triethoxy caprylylsilane (Kobopearl Interval Gold-11S2 from Kobo Products Inc.) | | | | | 0.75 |
| Mica/Titanium Dioxide/Triethoxy caprylylsilane (Kobopearl Stellar White-11S2 from Kobo Products Inc.) | | | 1.5 | | |

The composition described above can be prepared by conventional formulation and mixing techniques. Prepare the cleansing phase composition by first adding citric acid into water at a 1:3 ratio to form a citric acid premix. Then, add the following ingredients into the main mixing vessel in the following sequence: water, Miracare SLB-354, sodium chloride, and preservatives. Start agitation of the main mixing vessel. In a separate mixing vessel, disperse polymer (N-Hance 3196) in water at 1:10 ratio to form a polymer premix. Add the completely dispersed polymer premix into the main mixing vessel with continuous agitation. Disperse PEG 90M (Polyox WSR 301) in water and then add to the main mixing vessel. Then, add the rest of the water, perfume, and Expancel into the batch. Keep agitation until a homogenous solution forms.

Prepare the lipid phase by adding petrolatum into a mixing vessel. Heat the vessel to 190° F. Then, add mineral oil with agitation. Add interference pigment (Titanium Dioxide/Mica/Silica/Dimethicone) and allow the vessel to cool down with slow agitation.

The cleansing and lipid phases are density matched to within 0.05 g/cm$^3$. Package both phases into a single container using conventional toothpaste-tube filler equipment. The sample stage spins the bottle during filling process to create a striped appearance. The stripe size is about 6 mm in width and 100 mm in length.

| Ingredient | wt % |
|---|---|
| I. Phase 1 | |
| Ammonium Laureth-3 Sulfate (25% Active) | 46.7 |
| Citric Acid Anhydrous | 1.76 |
| Sodium Lauroamphoacetate (27%) | 43.47 |
| Trihydroxystearin (Thixcin R from Rheox) | 2.35 |

| Ingredient | wt % |
|---|---|
| Preservatives | 1.73 |
| Lauric Acid | 2.35 |
| Petrolatum | 1.64 |
| II. Phase 2 | |
| Ammonium Laureth-3 Sulfate | 18 |
| Ammonium Lauryl Sulfate (25% Active) | 12 |
| Phase 1 | 42.6 |
| Fragrance | 1.0 |
| Premix 1 | |
| Guar Hydroxypropyltrimonium Chloride (N-Hance 3196 from Aqualon) | 0.3 |
| Water | QS |
| Premix 2 | |
| Petrolatum | 17.3 |
| Titanium Dioxide/Mica/Silica/Dimethicone (SAT-Timiron Splendid Red from US Cosmetics) | 1.5 |

The composition described above can be prepared by conventional formulation and mixing techniques. Prepare Phase 1 by first adding citric acid into the ammonium laureth-3 sulfate. Once the citric acid is full dissolved, add the sodium lauroamphoacetate. Heat the mixture to 190-195 F. Incorporate the trihydroxystearin fully and then add preservatives. Continue to mix as petrolatum is added. Prepare Phase 2 in a separate mixing vessel. Add ammonium laureth-3 sulfate then ammonium lauryl sulfate to mixing vessel in a water bath. To this vessel add Phase 1 with continuous mixing. Premix the guar hydroxypropyl trimonium chloride and water (Premix 1). Add Premix 1 to mixing vessel. Prepare Premix 2 by adding petrolatum into a separate mixing vessel. Heat the vessel to 190° F. Add SAT-Timiron Splendid Red and allow to mix well. Then add Premix 2 to Phase 2. Then add perfume. Keep agitation until a homogenous solution forms.

| Ingredient | Ex. 19 wt % | Ex. 20 wt % | Ex. 21 wt % | Ex. 22 wt % | Ex. 23 wt % | Ex. 24 wt % | Ex. 25 wt % |
|---|---|---|---|---|---|---|---|
| I. Aqueous Phase Composition | | | | | | | |
| Hydroxypropyl Starch Phosphate (Structure XL from National Starch) | 3.5 | 4.0 | 3.5 | 3.5 | 3.5 | 3.0 | 3.5 |
| Emulsifying Wax NF (Polawax from Croda) | 2.75 | 3.0 | 2.75 | | 2.75 | 2.5 | |
| Behenetrimonium methosulfate and cetearyl alcohol (Incroquat Behenyl TMS from Croda) | | | | 2.25 | | | 2.0 |
| Fragrance | 1.0 | 1.0 | 1.0 | 1.0 | 1.0 | 1.0 | 1.0 |
| Preservatives | 0.8 | 0.8 | 0.8 | 0.8 | 0.8 | 0.8 | 0.8 |
| Water | Q.S. | Q.S. | Q.S. | Q.S. | Q.S. | Q.S. | Q.S. |
| II. Lipid/HMIP phase Composition | | | | | | | |
| Petrolatum (Superwhite Protopet from WITCO) | 15 | | | 5 | 15 | 15 | |
| Mineral Oil (Hydrobrite 1000 PO White MO from WITCO) | | 20 | | | | 2 | |
| Dimethicone Fluid (Dow Corning Silicone Fluid 10000 cst) | | | 10 | | | | 5 |
| Puresyn 101LT (Polydecene from Exxon Mobile) | | | | 15 | | | |
| Sunflower Seed Oil (Lipovol Sun from Lipo) | | | | | 10 | | |
| Mica/Titanium Dioxide/Dimethicone (SAT-Timiron MP115 Starluster from US Cosmetics) - 10% Dimethicone modification | 0.75 | | | | 0.2 | 0.5 | 0.5 |
| Mica/Titanium Dioxide/Triethoxy caprylylsilane/Iron Oxide/Tin Oxide (Kobopearl Vibrant Gold-11S2 from Kobo Products Inc.) 6% triethoxy caprylsilane modification | | 0.5 | | | | | 0.5 |

| Ingredient | Ex. 19 wt % | Ex. 20 wt % | Ex. 21 wt % | Ex. 22 wt % | Ex. 23 wt % | Ex. 24 wt % | Ex. 25 wt % |
|---|---|---|---|---|---|---|---|
| Mica/Titanium Dioxide/Triethoxy caprylylsilane (Kobopearl Stellar White-11S2 from Kobo Products Inc.) 8% Triethoxy caprylsilane modification | | | | 1.5 | | | 0.1 |
| Titanium Dioxide/Mica/Silica/Dimethicone (SAT-Timiron Splendid Red from US Cosmetics) 15% dimethicone modification | | 0.9 | | | | | 0.25 |
| Mica/Titanium Dioxide/Tin Oxide/Triethoxy caprylylsilane (Kobopearl Interval Gold-11S2 from Kobo Products Inc.) 12% Triethoxy caprylsilane modification | | | 0.5 | | | | |
| Mica/Titanium Dioxide/Tin Oxide/Triethoxy caprylylsilane (Kobopearl Interval Red-11S2 from Kobo Products Inc.) 10% Triethoxy Caprylsilane modification | | | | | | 1.0 | |

The personal care composition of Example 19-25 can be prepared by conventional formulation and mixing techniques.

Prepare the aqueous phase composition by first dispersing the hydroxypropyl starch phosphate in water. Add and heat the emulsifying wax is to 160 F. Next, Place the mixing vessel in a water bath to cool to under 100 F. Add fragrance.

Prepare the lipid phase by first premixing the HMIP(s) if necessary. Then, add the HMIP(s) to the lipid to the premix at 160 F. Then, add the lipid/HMIP phase to the aqueous phase (<80 F) with increased agitation. Add preservatives and agitate until product is smooth.

The following examples further describe and demonstrate embodiments within the scope of the Pigment Deposition Tape Strip Method. The Method can be used to semi-quantitatively determine deposition of shiny particles onto keratinous surfaces. The method employs the use of a tape strip for removing particles from skin and imaging these particles for a quantitation of deposited particles.

The following examples further describe and demonstrate embodiments within the scope of the Pigment Deposition Tape Strip Method. The Method can be used to semi-quantitatively determine deposition of shiny particles onto keratinous surfaces. The method employs the use of a tape strip for removing particles from skin and imaging these particles for a quantitation of deposited particles.

| Ingredient | Ex. 1 wt % | Ex. 2 wt % | Ex. 3 wt % | Ex. 4 wt % |
|---|---|---|---|---|
| I. Aqueous Phase Composition | | | | |
| Hydroxypropyl Starch Phosphate (Structure XL from National Starch) | 3.5 | 3.5 | 4.0 | 3.5 |
| Emulsifying Wax NF (Polawax from Croda) | 2.75 | 2.75 | 3.0 | 2.75 |
| Fragrance | 1.0 | 1.0 | 1.0 | 1.0 |
| Preservatives | 0.8 | 0.8 | 0.8 | 0.8 |
| Water | Q.S. | Q.S. | Q.S. | Q.S. |
| II. Lipid/HMIP phase Composition | | | | |
| Petrolatum (Superwhite Protopet from WITCO) | 20 | 15 | 15 | 14 |
| Mineral Oil (Hydrobrite 1000 PO White MO from WITCO) | 5 | | | 6 |
| Mica/Titanium Dioxide/Dimethicone (SAT-Timiron MP115 Starluster from US Cosmetics) | 0.75 | | 0.5 | 0.75 |
| Titanium Dioxide/Mica/Silica/Dimethicone (SAT-Timiron Splendid Red from US Cosmetics) | 0.75 | | 0.5 | 0.75 |
| Mica/Titanium Dioxide/Dimethicone (SAT-Timiron Super Green from US Cosmetics) | | 1.0 | | |
| Tape Stripping Method Results ($\mu g/cm^2$) | 40 | 25 | 25 | 40 |

The personal care composition of Example 1-4 can be prepared by conventional formulation and mixing techniques.

Prepare the aqueous phase composition by first dispersing the hydroxypropyl starch phosphate in water. Add and heat the emulsifying wax to 160 F. Next, Place the mixing vessel in a water bath to cool to under 100 F. Add fragrance.

Prepare the lipid phase by first premixing the HMIP(s) if necessary. Then, add the HMIP(s) to the lipid to the premix at 160 F. Then, add the lipid/HMIP phase to the aqueous phase (<80 F) with increased agitation. Add preservatives and agitate until product is smooth.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A personal care composition for use on skin comprising,
   a) a hydrophobically modified interference pigment, wherein said hydrophobically modified interference pigment comprises a mica substrate coated with $TiO_2$ and further comprises a silane hydrophobic coating, wherein said hydrophobically modified interference pigment comprises about 0.1 to about 20 weight percent of said silane hydrophobic coating;
   b) a dispersed oil phase; and
   c) a continuous aqueous phase;
   wherein said composition deposits at least 0.5 $\mu g/cm^2$ of said hydrophobically modified interference pigment on the skin.

2. The composition of claim 1, wherein said hydrophobically modified interference pigment has a refractive index of at least 1.8.

3. The composition of claim 1, wherein said hydrophobically modified interference pigment has a contact angle of at least 60 degrees.

4. The composition of claim 1, wherein said hydrophobically modified interference pigment has a contact angle of greater than 100 degrees.

5. The composition of claim 1, wherein said dispersed oil phase is selected from the group consisting of petrolatum, mineral oil, silicone, triglycerides, esters and mixtures thereof.

6. The composition of claim 1, wherein said aqueous phase is water.

7. The composition of claim 1, wherein said hydrophobically modified interference pigment is entrapped within said dispersed phase.

8. The composition of claim 1, comprising one or more benefit agents selected from the group consisting of vitamins, sunscreens, thickening agents, preservatives, anti-acne medicaments, antioxidants, skin soothing and healing agents, chelators and sequestrants, fragrances, essential oils, skin sensates, pigments, pearlescent agents, lakes, colorings, antibacterial agents and mixtures thereof.

9. The composition of claim 1, wherein said hydrophobically modified interference pigment is a platelet particulate having a thickness from about 0.2 μm to about 5 μm and an average diameter from about 0.1 μm to about 200 μm.

10. The composition of claim 1, wherein said composition comprises a plurality of hydrophobically modified interference pigments, and wherein the ratio of said hydrophobically modified interference pigments to said dispersed oil phase is about 1:7 to about 1:35.

11. A personal care composition for use on skin comprising,
   a) a hydrophobically modified interference pigment, wherein said hydrophobically modified interference pigment is a platelet particulate having a thickness from about 0.2 μm to about 5 μm and an average diameter from about 0.1 μm to about 200 μm, and further comprises a mica substrate coated with $TiO_2$ and further comprises a silane hydrophobic coating wherein said hydrophobically modified interference pigment comprises about 0.1 to about 20 weight percent of said silane hydrophobic coating
   b) a dispersed oil phase; and
   c) a continuous aqueous phase;
   wherein said composition deposits at least 0.5 $\mu/cm^2$ of said hydrophobically modified interference pigment on the skin.

12. The composition of claim 11, wherein said hydrophobically modified interference pigment has a refractive index of at least 1.8.

13. The composition of claim 11, wherein said hydrophobically modified interference pigment has a contact angle of at least 60 degrees.

14. The composition of claim 11, wherein said hydrophobically modified interference pigment has a contact angle of greater than 100 degrees.

15. The composition of claim 11, wherein said dispersed oil phase is selected from the group consisting of petrolatum, mineral oil, silicone, triglycerides, esters and mixtures thereof.

16. The composition of claim 11, wherein said aqueous phase is water.

17. The composition of claim 11, wherein said hydrophobically modified interference pigment is entrapped within said dispersed phase.

18. The composition of claim 11, comprising one or more benefit agents selected from the group consisting of vitamins, sunscreens, thickening agents, preservatives, anti-acne medicaments, antioxidants, skin soothing and healing agents, chelators and sequestrants, fragrances, essential oils, skin sensates, pigments, pearlescent agents, lakes, colorings, antibacterial agents and mixtures thereof.

19. The composition of claim 11, wherein said composition comprises a plurality of hydrophobically modified interference pigments, and wherein the ratio of said hydrophobically modified interference pigments to said dispersed oil phase is about 1:7 to about 1:35.

20. The composition of claim 11, wherein said oil phase comprises oil particles, and wherein said composition comprises less than 20 hydrophobically modified interference pigments per oil particle.

21. The composition of claim 1, wherein said hydrophobically modified interference pigment comprises about 1 to about 10 weight percent of said silane hydrophobic coating.

22. The composition of claim 11, wherein said hydrophobically modified interference pigment comprises about 1 to about 10 weight percent of said silane hydrophobic coating.

* * * * *